(12) United States Patent
Mukhopadhyay et al.

(10) Patent No.: US 7,071,367 B1
(45) Date of Patent: Jul. 4, 2006

(54) DIRECT ONE-STEP SYNTHESIS OF CF$_3$-I

(75) Inventors: Sudip Mukhopadhyay, Buffalo, NY (US); Hsueh Sung Tung, Getzville, NY (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 11/007,919

(22) Filed: Dec. 9, 2004

(51) Int. Cl.
C07C 17/00 (2006.01)

(52) U.S. Cl. .................. 570/101; 570/123; 570/170
(58) Field of Classification Search ............... 570/101, 570/123, 170
See application file for complete search history.

(56) References Cited

U.S. PATENT DOCUMENTS

| | | | |
|---|---|---|---|
| 4,794,200 A | 12/1988 | Tordeux et al. | ............. 570/170 |
| 4,922,041 A * | 5/1990 | Naumann et al. | ............ 570/141 |
| 5,892,136 A * | 4/1999 | Nagasaki et al. | ............ 570/174 |

FOREIGN PATENT DOCUMENTS

| | | |
|---|---|---|
| DE | 1805457 | 10/1968 |
| DE | 19751551 | 5/1988 |
| EP | 0266281 | 5/1988 |
| FR | 2794456 | 5/1999 |
| JP | 52068110 | 6/1977 |
| JP | 2262529 | 10/1999 |

OTHER PUBLICATIONS

Naumann, *Preparation and Properties of ZnBr(CF$_3$)-2L—A Convenient Route for the preparation of CF$_3$I*, Journal of Fluorine Chemistry, 67 (1994) 91-93.
Abstract: Tordeux, *Process for the preparation of trifluoromethyl iodide*, Rhone-Poulenc Chimie SA.
Abstract: Lee, *Synthesis of CF$_3$I by direct iodiniation of CF$_3$COOH on solid catalyst*, Waste Research Team, Energy & Environment Department, Taejou S. Korea, 2002.
Abstract: Su, *A simple, novel method for the preparation of trifluoromethyl iodide and diiododifluoromethane*, Journal of the Chemical Society, 1992.
Abstract: Chiriac, *Synthesis and purification of iodotrifluoromethane, bromotrifluoromethane, trifluoromethane-dl for laser isotope separation*, Revistade Chimie, Bucharest, Romania, 1982.
Abstract: Nagasaki, *Study on a novel catalytic reaction and its mechanism for CF$_3$I synthesis*, Research Laboratory, Tosoh F-Tech, Inc., Yamaguchi, Japan, 2004.
Dhooge, *Low Environmental Impact, High Performance Foam Blowing Agents Based on Iodofluorocarbons*, Environmental Technology and Education Center, Albuquerque, New Mexico.
Nagasaki, *The Development of a Novel Catalytic Technology for CF3I Manufacture*, Research Laboratory, Tosoh F-Tech, Inc., Yamaguchi, Japan.
Glass, *Gas Phase Combustion Suppression of Various Fuels by CF$_3$I*, Environmental Technology and Education Center, Albuquerque, New Mexico, 1999.

* cited by examiner

*Primary Examiner*—Johann Richter
*Assistant Examiner*—Chukwuma Nwaonicha
(74) *Attorney, Agent, or Firm*—Colleen D. Szuch

(57) ABSTRACT

The present invention provides a process for the preparation of trifluoromethyl iodide. The process includes the step of: contacting in a reactor a compound represented by the formula:

$$CF_3-W$$

and a compound represented by the formula:

$$Z-I$$

wherein W is selected from CF$_3$, hydrogen and bromine; Z is selected from hydrogen, iodine and chlorine. The step of contacting is carried out, optionally in the presence of a catalyst and further optionally in the presence of air, at a temperature, pressure and for a length of time sufficient to produce the trifluoromethyl iodide.

26 Claims, No Drawings

DIRECT ONE-STEP SYNTHESIS OF CF$_3$-I

BACKGROUND OF THE INVENTION

1. Field of the Invention

The present invention generally relates to a process for the preparation of trifluoromethyl iodide. More particularly, the present invention relates to a process for the preparation of trifluoromethyl iodide from CF$_3$—W and Z-I wherein W is CF$_3$, hydrogen or bromine and Z is hydrogen, iodine or chlorine.

2. Description of the Prior Art

An article by Dhooge et al. in Proceedings of the 4th Conference on Aerospace Materials, Processes, and Environmental Technology, page 259–268 (2000), describes vapor phase production process for the preparation of CF$_3$I by the reaction between CHF$_3$ with I$_2$ in the presence of a catalyst including alkali metal salts supported on an activated carbon carrier. The reaction mechanism appears to proceeds via CF$_2$ carbenes formed on the catalyst surface as intermediates, followed by carbene disproportionation to CF$_3$ radicals, followed by reaction with I$_2$ to give CF$_3$I (see Nagasaki, Noritaka et al., Catalysis Today (2004), 88(3–4), 121–126).

JP 52068110 (1977) describes the preparation of CF$_3$I by vapor-phase reaction of Freon 23 with iodine in the presence of alkali or alkaline earth metal salts.

DE 1805457 (1970) describes the preparation of CF$_3$I and C$_2$F$_5$I from the reaction of corresponding bromides and KI without solvent.

Naumann et al., J. Fluorine Chem., 67(1), 91–3(1994) describes the preparation of CF$_3$I from CF$_3$Br by a multi-step reaction, which employs elemental Zn.

European Patent Application EP 266,281 A1 (1988) describes the preparation of CF$_3$I from CF$_3$Br by contact with a metal or an alkali metal dithionite and SO$_2$ followed by treatment with iodine in a carboxylic or sulfonic acid.

Lee, K. -H. et al., Hwahak Konghak, 39(2), 144–149 (2001) describes the preparation of CF$_3$I by iodination of CF$_3$CO$_2$H with iodine using a flow reactor over various salt-impregnated catalysts.

Su, D. et al., J. Chem. Soc., Chem. Commun. (11), 807–8 (1992) describes the preparation of CF$_3$I by treatment of XCF2CO2Me (X=Cl or Br) with iodine in the presence of potassium fluoride and copper (I) iodide.

Chiriac, M. et al., Inst. Tehnol. Izot. Mol., 33(11), 1018–20 (1982) describes the preparation of CF$_3$I from Ag-trifluoroacetate.

However, in view of the high cost of the raw materials required and the formation of solid by-products that are difficult to dispose of because of their adverse impact on the environment, none of these methods provide a practical and economical process which could be adapted to large scale process for the preparation of CF$_3$I.

Furthermore, there is no report in the literature of any catalytic vapor-phase process for making CF$_3$I in high yield. Therefore, a high yield, catalytic vapor-phase process, which avoids the formation of solid by-products and the adverse impact of such solid by-products on the environment would be welcome by the Chemical Industry.

The above described problems can be avoided by the use of a process for the preparation of trifluoromethyl iodide from CF$_3$—W and Z-I wherein W is CF$_3$, hydrogen or bromine and Z is hydrogen, iodine or chlorine according to the present invention.

SUMMARY OF THE INVENTION

In broad concept, the present invention provides a process for the preparation of trifluoromethyl iodide. The process includes the step of:

contacting in a reactor a compound represented by the formula:

CF$_3$—W and a compound represented by the formula:

Z-I wherein W is selected from CF$_3$, hydrogen and bromine; Z is selected from hydrogen, iodine and chlorine. The step of contacting is carried out, optionally in the presence of a catalyst and further optionally in the presence of air, at a temperature, pressure and for a length of time sufficient to produce the trifluoromethyl iodide.

The present invention has the advantage of providing high yields and high purity trifluoromethyl iodide while avoiding the formation of solid by-products and their adverse impact on the environment.

These and other benefits of the present process will become more evident from the detailed description of the invention that follows.

DETAILED DESCRIPTION OF THE INVENTION

The present invention provides a process for the preparation of trifluoromethyl iodide from CF$_3$—W and Z-I wherein W is CF$_3$, hydrogen or bromine and Z is hydrogen, iodine or chlorine.

CF$_3$I is a non-toxic, non-flammable, low global warming potential compound with almost zero ozone depletion potential (See, for example, Dhooge et al., Proceedings of the 4th Conference on Aerospace Materials, Processes, and Environmental Technology, page 259–268 (2000)).

In addition, the life cycle of the CF$_3$I in the atmosphere is only about two days. Therefore, the Chemical Industry has a substantial incentive to produce this compound by a low-cost and environmentally acceptable route for use as a refrigerant either alone or in combination with other known or existing refrigerants.

Accordingly, the present invention provides a catalytic process, which uses low cost feedstocks, such as, CHF$_3$ and Iodine or Hydrogen Iodide as the starting materials to produce CF$_3$I with high selectivity.

As mentioned herein above, the processes described in the prior art generally are limited to lab-scale demonstration. Furthermore, the raw materials used in these methods are not readily available or expensive. Therefore, a substantial incentive exists for the development of alternative commercial processes for the manufacture of CF$_3$I.

Accordingly, the present invention provides herein a commercially useful catalytic process to achieve these objectives.

PREFERRED EMBODIMENTS

In a one preferred embodiment, W is hydrogen and Z is iodine (1a and 1b), wherein the process proceeds at least in part according to the following equation:

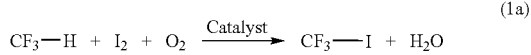
(1a)

or at least in part according to the following equation:

(1b)

In another preferred embodiment, W is bromine and Z is iodine (2a), wherein the process proceeds according to the following equation:

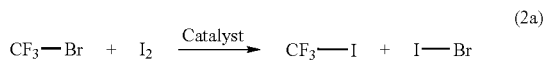
(2a)

In still another preferred embodiment, W is bromine and Z is hydrogen (2b), wherein the process proceeds according to the following equation:

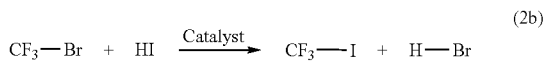
(2b)

In yet another preferred embodiment, W is bromine and Z is chlorine (2c), wherein the process proceeds according to the following equation:

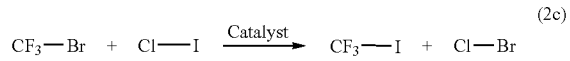
(2c)

In still another preferred embodiment, W is hydrogen and Z is hydrogen (3a or 3b), wherein the process proceeds at least in part according to the following equation:

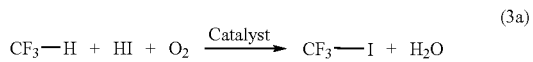
(3a)

or according to the following equation:

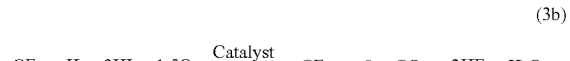
(3b)

In yet another embodiment, W is hydrogen and Z is chlorine (4a), wherein the process proceeds, with or without $O_2$, at least in part according to the following equation:

(4a)

In still another embodiment, W is $CF_3$ and Z is iodine (5a), wherein the process proceeds, with or without $O_2$, at least in part according to the following equation:

$$CF_3-CF_3+I_2 \rightarrow 2CF_3-I \qquad (5a)$$

In still a further embodiment, W is $CF_3$ and Z is hydrogen (5b), wherein the process proceeds, with or without $O_2$, at least in part according to the following equation:

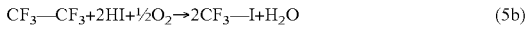

$$CF_3-CF_3+2HI+\tfrac{1}{2}O_2 \rightarrow 2CF_3-I+H_2O \qquad (5b)$$

Process Conditions:

In the practice of the process of the present invention, the step of contacting is preferably carried out at a temperature from about 20° C. to about 650° C., at a pressure from about 1 atm to about 100 atm, and for a length of time from about 0.01 sec to about 300 hours.

The process can be either a batch process or it can be a continuous process.

The reactor can further comprise a diluent, such as, a gas, a solvent or a mixture thereof. When the diluent is a gas, the diluent can be nitrogen, helium, argon or a mixture thereof. When the diluent is a solvent, the diluent is a solvent, which is preferably a liquid fluorocarbon.

The process can further include one or more of the following steps:

(1) passing the trifluoromethyl iodide through a scrubber containing an aqueous alkali solution;

(2) passing the trifluoromethyl iodide through a scrubber containing a drying agent;

(3) cooling at a temperature below the boiling temperature of the trifluoromethyl iodide to condense; and (4) isolating the trifluoromethyl iodide from the reaction mixture in substantially pure form.

In operation, preferably at least 10 wt % of the reactants are converted to trifluoromethyl iodide. More preferably, at least 80 wt % of the reactants are converted to trifluoromethyl iodide, and most preferably, at least 95 wt % of the reactants are converted to trifluoromethyl iodide.

The following non-limiting examples are illustrative of the various embodiments of the present invention. It is within the ability of a person of ordinary skill in the art to select other variable from among the many known in the art without departing from the scope of the present invention. Accordingly, these examples shall serve to further illustrate the present invention, not to limit them.

Unless otherwise indicated, all parts and percentages are on a weight basis.

EXAMPLE 1

One-Step Synthesis of $CF_3I$ from $CHF_3$ $CF_3I$ is synthesized in a cost-effective way by reacting $CHF_3$ with $I_2$ and $O_2$ (or Air) in the presence of a catalyst including one or more iodide, nitrate, oxide, bromide, carbonate, chloride, acetate, acetylacetonate salts of Cu (II), Hg (II), Pt (II), Pd (II), Co (III), Mn (III), Rh (III), Ni (II), V (IV), TI (III), and Ge (III) at 50–600° C. in a vapor or liquid-phase process.

The catalyst salts can be used directly (100 wt %) or a portion (2–60 wt %) on an active support such as activated carbon, alumina, $SiO_2$, or $ZrO_2$.

A mixture of salts supported on an active carbon, alumina, glass, SiO2, SBA-15 support can also be used to obtain higher selectivity to $CF_3I$ formation.

Thus, 20 SCCM (Standard Cubic Centimeter Per Minute) of $CHF_3$ is passed through a 50 cc 2 wt % Cu-5 wt % Pd-3 wt % Pt/C catalyst bed placed in a ½-inch Monel reactor in the presence of 20 SCCM of air or $O_2$ and 20 SCCM of Iodine at 550° C. to yield 40–95 mol % of $CF_3I$. The product mixture is analyzed by GC and GCMS.

Stoichiometric amount of $O_2$ is necessary for a thermodynamically favorable pathway (Eq 1) as written below because without the presence of $O_2$ the reaction is not favorable (Eq 2):

$$2CHF_3+I_2+\tfrac{1}{2}O_2 \rightarrow 2CF_3I+H_2O, \Delta G=-158 \text{ kJ/mol} \quad (Eq\ 1)$$

$$CHF_3+I_2 \rightarrow CF_3I+HI, \Delta G=+73.06 \text{ kJ/mol} \quad (Eq\ 2)$$

The reaction of $CHF_3$, $I_2$ and $O_2$ can also go in a different pathway as written below:

$$3CHF_3+I_2+O_2 \rightarrow 2CF_3I+CO_2+3HF, \Delta G=-397 \text{ kJ/mol} \quad (Eq\ 3)$$

Eq 1 and 3 are both possible on the same active catalyst site, thus, the overall rate of $CF_3I$ production will be the sum total of the rate of Eq 1 and Eq 3.

$CHF_3$, which is a common byproduct from fluorocarbon industries, can also be synthesized easily by vapor phase reaction of HF with $CHCl_3$ in the presence of a chromium oxide based catalyst at 200–450° C. Thus, the overall process is highly cost effective.

EXAMPLE 2

Preparation of $CF_3I$ by Oxidative Iodination of $CHF_3$ $CF_3I$ is synthesized in a cost-effective way by reacting $CHF_3$ with HI and $O_2$ (or Air) in the presence of a catalyst including one or more iodide, nitrate, oxide, bromide, carbonate, chloride, acetate, acetylacetonate salts of Mn (III), V (IV), Cr (III), Mo, Co (III), TI (III), and Ge (III) at 50–600° C. in a vapor phase process. The catalyst salts can be used directly (100 wt %) or a portion (2–60 wt %) on an active support such as activated carbon, alumina, $SiO_2$, and $ZrO_2$.

A mixture of salts can be used alone (100 wt %) or it can be supported on an active support to obtain higher selectivity to $CF_3I$ formation.

Thus, 20 SCCM of $CHF_3$ and 20 SCCM of HI are passed through a 50 cc $V_2O_5$ or Pd—Pt/C catalyst bed placed in a 1-inch Monel reactor in the presence of 20 SCCM of air or $O_2$ and at 500° C. to yield 67% of $CF_3I$. The product mixtures are analyzed by GC and GCMS.

Stoichiometric amount of $O_2$ is necessary for a thermodynamically favorable pathway (Eq 5) as written below because without the presence Of $O_2$ the reaction is not favorable (Eq 4):

$$CHF_3+HI \rightarrow CF_3I+H_2, \Delta G=+90.26 \text{ kJ/mol} \quad (Eq\ 4)$$

$$CHF_3+HI+\tfrac{1}{2}O_2 \rightarrow CF_3I+H_2O, \Delta G=-107.1 \text{ kJ/mol} \quad (Eq\ 5)$$

The reaction of $CHF_3$, HI and $O_2$ can also proceed in a more favorable pathway (Eq 6) as written below:

$$3CHF_3+2HI+1.5O_2 \rightarrow 2CF_3I+CO_2+3HF+H_2O, \Delta G=-668.5 \text{ kJ/mol} \quad (Eq\ 6)$$

$CHF_3$, which is a common by-product from fluorocarbon industries, can also be synthesized easily by the vapor phase reaction of HF with $CHCl_3$ in the presence of a chromium oxide based catalyst at 200–450° C. Thus, the overall process is highly cost effective.

EXAMPLE 3

Catalytic One-Step Synthesis of $CF_3I$ from $CHF_3$ $CF_3I$ is synthesized in a cost-effective manner by reacting $CHF_3$ with $Br_2$ and HI in the presence of any one or a mixture of the following iodide, nitrate, oxide, bromide, carbonate, chloride, acetate, acetylacetonate salts, and preferably oxide salts, of Cu, Pt, Pd, Co, Mn, Rh, Ni, V, TI, Th, Ge, and Cr, at 10–600° C. in a vapor or liquid-phase process (Eq 1).

The catalyst salts can be used directly (100 wt %) or a portion (2–60 wt %) on an active support such as activated carbon, alumina $SiO_2$, and $ZrO_2$.

A mixture of salts supported on an active support can also be used to obtain higher selectivity to $CF_3I$ formation.

The reaction can be written as:

$$CHF_3+Br_2+HI \rightarrow CF_3I+2HBr, \Delta G=-19.3 \text{ kJ/mol} \quad (Eq\ 7)$$

$CHF_3$, which is a common byproduct from fluorocarbon industries, can also be synthesize easily by the vapor phase reaction of 3 moles of HF with one mole of $CHCl_3$ in the presence of a chromium oxide based catalyst at 200–450° C. Thus, the overall process is highly cost effective.

Thus, 20 SCCM of $CHF_3$, 20 SCCM of Bromine and 30 SCCM of Iodine or HI were passed through a 50 cc Pd/C bed placed in a ½-inch Monel reactor to yield 70 mol % of $CF_3I$ at 500° C. The reactor pressure was kept at 50 psig. The product mixtures exiting the reactor were analyzed by an on-line GC and GCMS couple.

EXAMPLE 4

Catalytic One-Step Synthesis of $CF_3I$ from $CHF_3$ $CF_3I$ can be synthesized in a cost-effective way by reacting $CHF_3$ with $Br_2$ and HI in the presence of any one or a mixture of the iodide, nitrate, oxide, bromide, carbonate, chloride, acetate, acetylacetonate salts, and preferably oxide salts, of Cu, Pt, Pd, Co, Mn, Rh, Ni, V, TI, Th, Ge, and Cr, at 10–600° C. in a vapor or liquid-phase process (Eq 8). The catalyst salts can be used directly (100 wt %) or a portion (2–60 wt %) on an active support such as activated carbon, alumina, $SiO_2$, and $ZrO_2$. A mixture of salts supported on an active support can also be used to obtain higher selectivity to $CF_3I$.

The reaction can be written as:

$$CHF_3+Br_2+HI \rightarrow CF_3I+2HBr, \Delta G=-19.3 \text{ kJ/mol} \quad (Eq\ 8)$$

$CHF_3$, which is a common byproduct from fluorocarbon industries, can also be synthesize easily by the vapor phase reaction of 3 moles of HF with one mole of $CHCl_3$ in the presence of a chromium oxide based catalyst at 200–450° C. Thus the overall process is highly cost effective.

EXAMPLE 5

Oxidative Iodination of $CHF_3$ to $CF_3I$ $CF_3I$ can be synthesized in a cost-effective way by reacting $CHF_3$ with HI and $O_2$ (or Air) in the presence of a catalyst including one or more iodide, nitrate, oxide, bromide, carbonate, chloride, acetate, acetylacetonate salts of Mn(III), V(IV), Cr(III), Mo, Co(III), TI(III), and Ge(III), at 50–600° C. in a vapor phase process. The catalyst salts can be used directly (100 wt %) or a portion (2–60 wt %) on an active support such as activated carbon, alumina, $SiO_2$, and $ZrO_2$. A mixture of salts can also be used alone (100 wt %)

as well as supported on an active support to obtain higher selectivity to CF$_3$I formation.

Stoichiometric amount of O$_2$ is necessary for a thermodynamically favorable pathway (Eq 10) as written below because without the presence Of O$_2$ the reaction is not favorable (Eq 9):

$$CHF_3 + HI \rightarrow CF_3I + H_2, \Delta G = +90.26 \text{ kJ/mol} \quad (Eq\ 9)$$

$$CHF_3 + HI + \tfrac{1}{2}O_2 \rightarrow CF_3I + H_2O, \Delta G = -107.1 \text{ kJ/mol} \quad (Eq\ 10)$$

The reaction of CHF$_3$, HI and O$_2$ can also go in a more favorable pathway (Eq 11) as written below:

$$3CHF_3 + 2HI + 1.5O_2 \rightarrow 2CF_3I + CO_2 + 3HF + H_2O, \Delta G = -668.5 \text{ kJ/mol} \quad (Eq\ 11)$$

CHF$_3$, which a common byproduct from fluorocarbon industries, can also be synthesize easily by the vapor phase reaction of HF with CHCl$_3$ in the presence of a chromium oxide based catalyst at 200–450° C. Thus the overall process is highly cost effective.

The present invention has been described with particular reference to the preferred embodiments. It should be understood that variations and modifications thereof can be devised by those skilled in the art without departing from the spirit and scope of the present invention. Accordingly, the present invention embraces all such alternatives, modifications and variations that fall within the scope of the appended claims.

What is claimed is:

1. A process for the preparation of trifluoromethyl iodide, comprising the step of:
   contacting in a reactor a compound represented by the formula:

CF$_3$—W and a compound represented by the formula:

Z-I wherein W is selected from the group consisting of CF$_3$, hydrogen and bromine; Z is selected from the group consisting of hydrogen, and chlorine; and wherein said step of contacting is carried out, optionally in the presence of a catalyst and further optionally in the presence of air, at a temperature, pressure and for a length of time sufficient to produce said trifluoromethyl iodide.

2. The process of claim 1, wherein W is bromine and Z is hydrogen.

3. The process of claim 1, wherein W is bromine and Z is chlorine.

4. The process of claim 1, wherein W is hydrogen and Z is hydrogen.

5. The process of claim 1, wherein W is hydrogen and Z is chlorine.

6. A process for the preparation of trifluoromethyl iodide, comprising the step of:
   contacting in a reactor a compound represented by the formula:

CF$_3$—W and a compound represented by the formula:

Z-I wherein W is CF$_3$ and Z is iodine; and wherein said step of contacting is carried out, optionally in the presence of a catalyst and further optionally in the presence of air, at a temperature, pressure and for a length of time sufficient to produce said trifluoromethyl iodide.

7. The process of claim 1, wherein W is CF$_3$ and Z is hydrogen.

8. The process of claim 1, wherein said step of contacting is carried out at a temperature from about 20° C. to about 650° C.

9. The process of claim 1, wherein said step of contacting is carried out at a pressure from about 1 atm to about 100 atm.

10. The process of claim 1, wherein said step of contacting is carried out for a length of time from about 0.01 sec to about 300 hours.

11. The process of claim 1, wherein the process is a batch process.

12. The process of claim 1, wherein the process is a continuous process.

13. The process of claim 1, wherein the reactor further comprises a diluent selected from the group consisting or a gas, a solvent and a mixture thereof.

14. The process of claim 13, wherein said gas is selected from the group consisting of: nitrogen, helium, argon and a mixture thereof.

15. The process of claim 13, wherein said solvent is a liquid fluorocarbon.

16. The process of claim 1, further comprising the step of:
   passing the trifluoromethyl iodide through a scrubber containing an aqueous alkali solution.

17. The process of claim 1, further comprising the step of:
   passing the trifluoromethyl iodide through a scrubber containing a drying agent.

18. The process of claim 1, further comprising the step of:
   cooling at a temperature below the boiling temperature of the trifluoromethyl iodide to condense.

19. The process of claim 1, further comprising the step of:
   isolating the trifluoromethyl iodide from the reaction mixture in substantially pure form.

20. The process of claim 1, wherein at least 10 wt % of the reactants are converted to trifluoromethyl iodide.

21. The process of claim 1, wherein at least 80 wt % of the reactants are converted to trifluoromethyl iodide.

22. The process of claim 1, wherein at least 95 wt % of the reactants are converted to trifluoromethyl iodide.

23. A process for the preparation of trifluoromethyl iodide, comprising the step of:
   contacting in a reactor a compound represented by the formula:

CF$_3$—W and a compound represented by the formula:

Z-I wherein W is hydrogen; Z is iodine; and wherein said step of contacting is carried out in the absence of a catalyst and absence of air, at a temperature, pressure and for a length of time sufficient to produce said trifluoromethyl iodide.

24. A process for the preparation of trifluoromethyl iodide, comprising the step of:
   contacting in a reactor a compound represented by the formula:

CF$_3$—W and a compound represented by the formula:

Z-I wherein W Is hydrogen; Z is iodine; and wherein said stop of contacting is carried out in the presence of one or more catalysts selected from the group consisting of iodide, nitrate, oxide, bromide, carbonate, chloride, acetate, acetylacetonate salts of Cu (II), Hg (II), Pt (II), Pd (II), Co (III), Mn (III), Rh (III), Ni (II), V (IV), TI (III), and Ge (III), and at a temperature, pressure and for a length of time sufficient to produce said trifluoromethyl iodide.

25. A process for the preparation of trifluoromethyl iodide, comprising the step of:

contacting in a reactor a compound represented by the formula:

$CF_3$—W and a compound represented by the formula:

Z-I wherein W is bromine; Z is iodine; and wherein said step of contacting is carried out in the absence of a catalyst and in the presence or absence of air, at a temperature, pressure and for a length of time sufficient to produce said trifluoromethyl iodide.

26. A process for the preparation of trifluoromethyl iodide, comprising the step of contacting in a reactor a compound represented by the formula:

$CF_3$—W and a compound represented by the formula:

Z-I wherein W is bromine; Z is iodine; and wherein said step of contacting is carried out in the presence of one or more catalysts selected from the group consisting of iodide, nitrate, oxide, bromide, carbonate, chloride, acetate, acetylacetonate salts of Cu (II), Hg (II), Pt (II), Pd (II), Co (III), Mn (III), Rh (III), Ni (II), V (IV), TI (III), and Ge (III), and at a temperature, pressure and for a length of time sufficient to produce said trifluoromethyl iodide.

* * * * *